United States Patent [19]

Murdock et al.

[11] Patent Number: 4,540,583

[45] Date of Patent: Sep. 10, 1985

[54] METHOD OF TREATING TUMORS IN WARM-BLOODED ANIMALS

[75] Inventors: Keith C. Murdock, Pearl River, N.Y.; Frederick E. Durr, Ridgewood, N.J.

[73] Assignee: American Cyanamid Company, Stamford, Conn.

[21] Appl. No.: 214,147

[22] Filed: Dec. 8, 1980

Related U.S. Application Data

[63] Continuation-in-part of Ser. No. 63,290, Aug. 2, 1979, abandoned, which is a continuation of Ser. No. 873,174, Jan. 30, 1978, abandoned.

[51] Int. Cl.³ .......................................... H61K 31/135
[52] U.S. Cl. .................................................. 514/656
[58] Field of Search ........................................ 424/330

[56] References Cited

U.S. PATENT DOCUMENTS 4,051,155  9/1977  Hoare ................................. 260/379

OTHER PUBLICATIONS

Chemical Abstracts 61:1977(e), (1964).
Simon, J. of Am. Chem. Soc., vol. 85, 7/5/63, pp. 1974–1977.

*Primary Examiner*—Jerome D. Goldberg
*Attorney, Agent, or Firm*—Edward A. Conroy, Jr.

[57] ABSTRACT

This disclosure describes novel compositions of matter useful as growth inhibitors of transplanted tumors in mammals and the method of inducing the regression and/or palliation of leukemia and solid tumors in mammals therewith, the active ingredients of said compositions of matter being certain symmetrical 1,4-bis(substituted-amino)anthraquinones and the non-toxic acid-addition salts thereof.

1 Claim, No Drawings

METHOD OF TREATING TUMORS IN WARM-BLOODED ANIMALS

CROSS REFERENCE TO RELATED APPLICATION

This application is a continuation-in-part of our co-pending application Ser. No. 63,290, filed Aug. 2, 1979, now abandoned, which is a continuation of our abandoned application Ser. No. 873,174, filed Jan. 30, 1978.

BRIEF SUMMARY OF THE INVENTION

This invention relates to novel compositions of matter useful for ameliorating cancer diseases in mammals. More particularly, it relates to therapeutic compositions of matter containing certain symmetrical 1,4-bis(substituted-amino)anthraquinones or the non-toxic acid-addition salts thereof which inhibit the growth of transplanted mammallian tumors. The 1,4-bis(substituted-amino)anthraquinones of the present invention may be represented by the following structural formula:

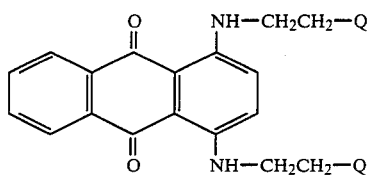

wherein Q is selected from the group consisting of amino, methylamino, ethylamino, dimethylamino, diethylamino, piperidino and morpholino.

Also included within the purview of the present invention are the leuco bases and tautomers thereof which may be represented by the following structural formulae wherein Q is as defined hereinabove:

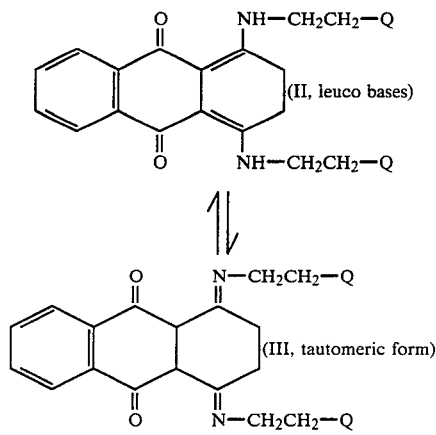

DETAILED DESCRIPTION OF THE INVENTION

The active compounds of the present invention are obtainable as reddish brown to blue black crystalline materials having characteristic melting points and absorption spectra and which may be purified by leaching with lower alkanols since the free bases are insoluble in water and some of them are insoluble in most organic solvents. The organic bases of this invention (I, II, and III) form non-toxic acid-addition salts with a variety of pharmacologically acceptable organic and inorganic salt-forming reagents. Thus, acid-addition salts, formed by admixture of the organic free base with two or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The active compounds of the present invention may be readily prepared in accordance with the following reaction scheme:

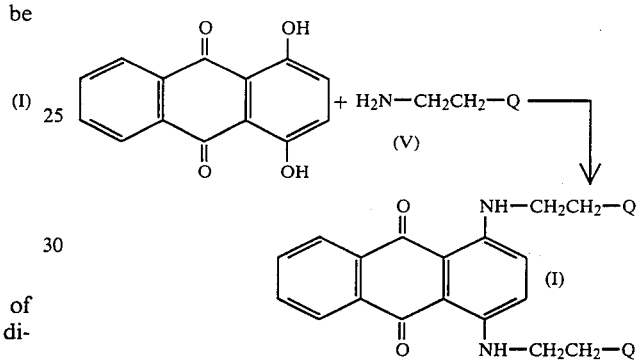

wherein Q is as hereinabove defined. In accordance with this reaction scheme, quinizarin (IV) (or leucoquinizarin) is condensed with the appropriate alkylene diamine (V) in water or N,N,N',N'-tetramethylethylenediamine as solvent at the reflux temperature for 1–15 hours to produce the corresponding bases. The leuco bases may be readily oxidized to the fully aromatic derivatives (I) by a variety of methods such as air oxidation or treatment with hot nitrobenzene, chloranil, hydrogen peroxide or sodium perborate.

The active compounds of the present invention possess the property of inhibiting the growth of transplanted mouse tumors as established by the following tests.

Lymphocytic leukemia P388 test (intraperitoneal)

The animals used are $BDF_1$ or $CDF_1$ mice, all of one sex, weighing a minimum of 17 grams and all within a 3-gram weight range. There are 5 or 6 animals per test group. The tumor transplant is by intraperitoneal injection of 0.1 ml. of dilute ascitic fluid containing $10^6$ cells of lymphocytic leukemia P388. The test compounds are administered intraperitoneally on days one, 5 and 9; or 1–9 (relative to tumor inoculation) at various doses. The animals are weighed and survivors are recorded on a regular basis for 30 days. The median survival time and the ratio of survival time for treated (T)/control (C) animals are calculated. The positive control compound is 5-fluorouracil, dosed at 60 mg./kg. of body weight. The results of this test with typical compounds of the present invention appear in Table I below. The criterion for efficacy is $T/C \times 100 \geqq 125\%$.

TABLE I

Lymphocytic leukemia P388 test

| Compound | Dose (mg./kg. of body weight) | Median Survival (Days) | T/C × 100 (Percent) | Administration |
|---|---|---|---|---|
| 1,4-Bis(2-dimethylaminoethylamino)-anthraquinone | 200 | 15.0 | 136 | Days 1, 5, and 9 |
|  | 100 | 18.5 | 168 |  |
|  | 50 | 15.0 | 136 |  |
| Control | 0 | 11.0 | — |  |
| 5-Fluorouracil | 60 | 18.5 | 168 |  |
| 1,4-Bis(2-morpholinoethylamino)-anthraquinone | 400 | 23.0 | 219 | Days 1-9 |
|  | 200 | 15.0 | 143 |  |
|  | 100 | 15.0 | 143 |  |
|  | 50 | 13.0 | 124 |  |
| Control | 0 | 10.5 | — |  |
| 5-Fluorouracil | 20 | 29.0 | 276 |  |
| 1,4-Bis(2-diethylaminoethylamino)-anthraquinone | 200 | 14.0 | 140 | Days 1, 5 and 9 |
|  | 100 | 12.0 | 120 |  |
|  | 50 | 13.0 | 130 |  |
| Control | 0 | 10.0 | — |  |
| 5-Fluorouracil | 60 | 17.5 | 175 |  |
| 1,4-Bis(2-piperidinoethylamino)-anthraquinone | 200 | 14.0 | 127 | Days 1, 5 and 9 |
|  | 100 | 12.0 | 109 |  |
|  | 50 | 11.0 | 100 |  |
| Control | 0 | 11.0 | — |  |
| 5-Fluorouracil | 60 | 19.0 | 173 |  |
| Leuco-1,4-bis(2-aminoethylamino)-anthraquinone | 200 | 27.0 | 245 | Days 1, 5 and 9 |
|  | 100 | 24.0 | 218 |  |
|  | 50 | 20.0 | 182 |  |
|  | 25 | 21.0 | 191 |  |
|  | 12 | 21.0 | 191 |  |
| Control | 0 | 11.0 | — |  |
| 5-Fluorouracil | 60 | 22.0 | 200 |  |
| 1,4-Bis(2-aminoethylamino)-anthraquinone | 25 | 22.0 | 244 | Days 1, 5 and 9 |
|  | 12 | 18.0 | 200 |  |
|  | 6 | 16.5 | 183 |  |
|  | 3 | 16.0 | 178 |  |
|  | 1.5 | 16.5 | 183 |  |
|  | 0.7 | 15.5 | 172 |  |
| Control | 0 | 9.0 | — |  |
| 5-Fluorouracil | 60 | 21.0 | 233 |  |
| 1,4-Bis(2-methylaminoethylamino)-anthraquinone | 12 | 22.0 | 244 | Days 1, 5 and 9 |
|  | 6 | 21.0 | 233 |  |
|  | 3 | 17.0 | 189 |  |
| Control | 0 | 9.0 | — |  |
| 5-Fluorouracil | 60 | 19.5 | 217 |  |

Lymphocytic leukemia P388 test (oral)

The procedure used is the same as for the previously described test for lymphocylic leukemia P388 except that the test compounds are administered orally at various doses rather than intraperitoneally. The results of this test with a typical compound of the present invention appear in Table II below. The criterion for efficacy is T/C × 100 ≧ 125%.

TABLE II

Lymphocytic leukemia P388 test (oral drug administration)

| Compound | Dose (mg./kg.) Days 1-9 | Median Survival (Days) | T/C × 100 (Percent) |
|---|---|---|---|
| 1,4-Bis-(2-dimethylaminoethylamino)-anthraquinone | 100 | 17.5 | 159 |
|  | 50 | 13.5 | 123 |
|  | 25 | 14.0 | 127 |
| Control | 0 | 11.0 | — |
| 5-Fluorouracil | 20 | 13.5 | 127 |

Lymphocytic leukemia L1210 test

The procedure is the same as for the lymphocytic leukemia P388 intraperitoneal test except that the tumor transplant consists of lymphocytic leukemia L1210 inoculated at a concentration of $10^5$ cells/mouse with a mean survival time being calculated. The results with a representative compound of this invention appear in Table III below.

TABLE III

Lymphocytic leukemia L1210 test

| Compound | Dose (mg./kg.) Days 1-9 | Mean Survival (Days) | T/C × 100 (Percent) |
|---|---|---|---|
| 1,4-Bis-(2-dimethylaminoethylamino)-anthraquinone | 50 | 12.0 | 135 |
|  | 25 | 11.0 | 124 |
|  | 12 | 9.4 | 106 |
| Control | 0 | 8.9 | — |
| 5-Fluorouracil | 20 | 17.6 | 188 |

Melanotic Melanoma B16

The animals used are C57BC/6 mice, all of the same sex, weighing a minimum of 17 grams and all within a 3-gram weight range. There are normally 10 animals per test group. A one-group portion of melanotic melanoma B16 tumor is homogenized in 10 ml. of cold balanced salt solution and implanted intraperitoneally into each of the test mice as a 0.5-ml. aliquot of the homogenate. The test compounds are administered intraperitoneally on days one through nine (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil. The results of this test with typical compounds of the present invention appear in Table IV below. The criterion for efficacy is $T/C \times 100 \geqq 125\%$.

TABLE IV

| Compound | Melanotic melanoma B16 | | |
|---|---|---|---|
| | Dose (mg./kg.) Days 1–9 | Median Survival (Days) | T/C × 100 (Percent) |
| 1,4-Bis- (2-dimethylaminoethylamino)- anthraquinone | 50 | 23.0 | 139 |
| | 25 | 19.5 | 118 |
| | 12 | 13.5 | 84 |
| Control | 0 | 16.5 | — |
| 5-Fluorouracil | 20 | 25.5 | 155 |
| 1,4-Bis- (2-morpholinoethylamino)- anthraquinone | 400 | 24.0 | 133 |
| | 200 | 20.0 | 111 |
| Control | 0 | 18.0 | — |
| 5-Fluorouracil | 20 | 26.0 | 144 |
| Leuco- 1,4-bis(2-aminoethylamino)- anthraquinone | 100 | 25.0 | 143 |
| | 50 | 35.5 | 203 |
| | 25 | 33.0 | 187 |
| | 12 | 27.5 | 157 |
| | 6 | 22.0 | 126 |
| Control | 0 | 17.5 | — |
| 5-Fluorouracil | 20 | 26.0 | 149 |
| 1,4-Bis(2-aminoethylamino)- anthraquinone | 12 | 31.0 | 182 |
| | 6 | 30.5 | 179 |
| | 3 | 29.0 | 171 |
| | 1.5 | 23.5 | 138 |
| | 0.7 | 22.0 | 129 |
| Control | 0 | 17.0 | — |
| 5-Fluorouracil | 20 | 26.0 | 153 |
| 1,4-Bis- (2-methylaminoethylamino)- anthraquinone | 12 | 33.0 | 187 |
| | 6 | 37.5 | 214 |
| | 3 | 36.0 | 206 |
| | 1.5 | 28.5 | 163 |
| | 0.7 | 24.5 | 140 |
| Control | 0 | 17.5 | — |
| 5-Fluorouracil | 20 | 26.0 | 149 |

It is obvious that the value of an animal tumor screen depends on its ability to select new drugs with efficacy against human cancer. In a study by the National Cancer Institute (reported by J. M. Venditti in a chapter in Pharmacological Basis of Cancer Chemotherapy, 1975, the Williams and Williams Co. entitled "Relevance of Transplantable Animal-Tumor Systems to the Selection of Transplantable Animal-Tumor Systems to the Selection of New Agents for Clinical Trial") it was concluded that the rodent tumors L1210, P388 and B-16 melanoma would have predicted the clinical activity of most of the established anticancer drugs. The retrospective analysis of 45 clinically active drugs also indicated that the predictive value of L1210 leukemia of mice extended to human solid tumors as well as human leukemias and lymphomas. Nineteen of the 21 human solid tumor active drugs met at least the minimal criteria of activity in the L1210 or P388 screens and thus would have been detected. The tumor systems used in the foregoing evaluation of the active compounds are the same tumor systems used by the National Cancer Institute for evaluation of potential anticancer drugs. The test protocols used are those established and recommended by the National Cancer Institute. It is recognized, however, that no single animal tumor or combination of tumors can predict perfectly therapeutic efficacy in man.

The active ingredients of the present invention inhibit transplanted mammalian tumor growth and induce regression and/or palliation of leukemia and related cancers in mammals when administered orally in amounts ranging from about 5 mg. to about 200 mg. per kilogram of body weight per day. A preferred dosage regimen for optimum results would be from about 5 mg. to about 50 mg. per kilogram of body weight per day, and such dosage units are employed that a total of from about 350 mg. to about 3.5 grams of the active compound for a subject of about 70 kg. of body weight are administered in a 24-hour period. This dosage regimen may be adjusted to provide the optimum therapeutic response. For example, several divided a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The active ingredients of the present invention may also be administered parenterally or intraperitoneally. The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The principal active ingredient is thus compounded for convenient and effective parenteral or intraperitoneal administration in effective amounts with a suitable pharmaceutically acceptable carrier in dosage unit form as hereinbefore disclosed. A dosage unit form contains the active ingredient in amounts ranging from about one to about 400 mg. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

The invention will be described in greater detail in conjunction with the following specific examples.

EXAMPLE 1

Preparation of 1,4-bis(2-dimethylaminoethylamino)anthraquinone

A mixture of 3 g. of quinizarin, 10 g. of N,N-dimethylethylenediamine and 17.5 ml. of water is stirred and heated under reflux for 3.5 hours. The mixture is cooled and the solid is collected and washed with water giving 2.96 g. of the desired product as a dark blue solid, mp. 170°–172° C.

Alternatively, the above product may be prepared by stirring and heating under reflux for 5 hours a mixture of 2.4 g. of quinizarin, 2.82 g. of N,N-dimethylethylenediamine and 9 ml. of N,N,N',N'-tetramethylethylenediamine. The product is recovered as described above.

EXAMPLE 2

Preparation of 1,4-bis(2-morpholinoethylamino)anthraquinone

A 9.60 g. portion of quinizarin, 46.90 g. of N-(2-aminoethyl)morpholine and 56 ml. of water are reacted as described in Example 1 giving 9.92 g. of the desired product as a blue-black solid, mp. 158°–159° C.

EXAMPLE 3

Preparation of 1,4-bis(2-diethylaminoethylamino)anthraquinone

A mixture of 42 ml. of N,N,N',N'-tetramethylenediamine, 17.43 g. of N,N-diethylethylenediamine and 12.01 g. of quinizarin is stirred and heated under reflux for 15 hours. The resulting solution is evaporated to dryness and a chloroform solution of the residue is filtered through 300 g. of alumina. The blue filtrate is chromatographed on silica gel in a Nylon ® film column, developing with a chloroform:methanol (6:1) mixture. The major blue band is cut out and then eluted with a chloroform:methanol:triethylamine (6:2:1) mixture. The eluate is evaporated. The residue is crystallized from hexane and washed with petroleum ether, giving 1.43 g. of the desired product as blue-black plates, mp. 109° C.

EXAMPLE 4

Preparation of leuco-1,4-bis(2-aminoethylamino)anthraquinone

A 125-ml. portion of ethylenediamine is de-aerated by bubbling nitrogen through it for 15 minutes. A 12.0-g. portion of leuco-quinizarin is added and the mixture is heated with stirring under nitrogen at 50° C. for one hour. The mixture is allowed to cool. The solid is collected and washed successively with ethyl acetate, acetonitrile and petroleum ether, giving 8.07 g. of the desired product as green-gold crystals, mp. 162°–165° C. (dec.) at a heating rate of 9° C. per minute.

EXAMPLE 5

Preparation of 1,4-bis(2-aminoethylamino)anthraquinone

Air is bubbled into a mixture of 7.0 g. of leuco-1,4-bis(2-aminoethylamino)anthraquinone and 87.5 ml. of ethylenediamine while heating at 50° C. for one hour. The mixture is diluted with 87.5 ml. of acetonitrile, allowed to cool and the solid is collected and washed with acetonitrile giving 5.43 g. of the desired product as a dark blue solid, mp. 170°–171° C.

EXAMPLE 6

Preparation of 1,4-bis(2-methylaminoethylamino)anthraquinone

A mixture of 2.4 g. of leuco-quinizarin and 25 g. of de-aerated N-methylethylenediamine is heated at 50° C. with stirring under nitrogen for one hour. Heating at 50° C. is continued as air is bubbled into the mixture for 40 minutes. The mixture is evaporated to dryness, then re-evaporated twice from 25 ml. portions of ethanol. Crystallization of the residue from ethanol-ether at −70° C. gives 2.32 g. of crude solid which is recrystallized twice from carbon tetrachloride giving 1.92 g. of the desired product as dark blue crystals, mp. 131°–132° C.

EXAMPLE 7

Preparation of 1,4-bis(2-piperidinoethylamino)anthraquinone

A mixture of 4.07 g. or quinizarin, 21.74 g. of N-(2-aminoethyl)piperidine and 26 ml. of water is stirred under reflux for 2 hours and then allowed to stand overnight. The gummy solid is collected and washed with water by centrifugation, giving 1.99 g. of blue-black solid. This solid is dissolved in 15 ml. of chloroform and chromatographed by an abbreviated wet-column procedure on 100 g. of alumina, eluting with chloroform. A total of 180 ml. of eluate is collected in eight separate cuts from the time the eluate turns blue until a black band nears the bottom of the column. Cuts 1–6 are combined and evaporated giving 1.42 g. of blue-black crystals which are recrystallized from ethanol giving 1.35 g. of the desired product as blue-black needles, mp. 140°–141° C. Product dried in vacuo at 78° C. melted at 156°–157° C.

EXAMPLE 8

Preparation of leuco-1,4-bis(2-dimethylaminoethylamino)anthraquinone

A solution of 26.44 g. of N,N-dimethylethylenediamine in 75 ml. of N,N,N',N'-tetramethylethylenediamine is de-aerated by bubbling through $N_2$ for 15 minutes. Then, 12.11 g. of leuco-quinizarin is added and the resulting mixture is stirred under $N_2$ while heating at 48°–50° C. for 21 hours. After cooling overnight under nitrogen, the solid is collected by filtration and washed three times by slurrying with acetonitrile and then twice with petroleum ether. There is thus obtained 12.52 g. of dark green crystals, mp. 150°–157° C.; or on the hot stage microscope, mp. 153°–154° C.

EXAMPLE 9

Preparation of 50 mg. Tablets

| Per Tablet | | Per 10,000 Tablets |
|---|---|---|
| 0.050 gm. | 1,4-bis(2-methylaminoethylamino)anthraquinone | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 1,4,-bis(2-methylaminoethylamino)anthraquinone, lactose and corn starch (for mix) are blended together. The corn starch (for paste) is suspended in 600 ml. of water and heated with stirring to form a paste. This paste is then used to granulate the mixted powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 10

Preparation of Oral Suspension

| Ingredient | Amount |
| --- | --- |
| Leuco-1,4-bis(2-aminoethylamino)anthraquinone | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water gs ad | 100 ml. |

The sorbitol solution is added to 40 ml. of distilled water and the leuco-1,4-bis(2-aminoethylamino)anthraquinone is suspended therein. The saccharin, sodium benzoate, flavor and dye are added and dissolved. The volume is adjusted to 100 ml. with distilled water. Each ml. of syrup contains 5 mg. of leuco-1,4-bis(2-aminoethylamino)anthraquinone.

EXAMPLE 11

Preparation of Parenteral Solution

In a solution of 700 ml. of propylene glycol and 200 ml. of water for injection is suspended 20.0 grams of 1,4-bis(2-ethylaminoethylamino)anthraquinone with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 12

Preparation of leuco-1,4-bis(2-ethylaminoethylamino)anthraquinone

Using 15.32 g. of 2-ethylaminoethylamine instead of N,N-dimethylethylenediamine in the procedure of Example 8 gives the title compound after the reaction time of one hour at 50°.

EXAMPLE 13

Leuco-1,4-bis(2-(2-methylaminoethylamino)ethylamino)anthraquinone

A solution of 14.10 g. (0.12 mole) of 1-methyl-diethylenetriamine in 100 ml. of ethanol is de-aerated by bubbling nitrogen through it for 15 minutes; then 9.69 g. (0.04) of leuco-quinizarin is added gradually with stirring. The mixture is stirred under nitrogen and heated with an oil bath at 50° C. for 21 hours. The mixture is allowed to cool, the product is collected by filtration and washed with acetonitrile and then with petroleum ether to give the title compound as a dark green solid.

EXAMPLE 14

Preparation of leuco-1,4,bis(2-methylaminoethylamino)anthraquinone

To a de-aerated (See Example 8) solution of 8.89 g. of N-methylethylenediamine in 80 ml. of N,N,N',N'-tetramethylethylenediamine is added 9.68 g. of leuco-quinizarin. The mixture is stirred and heated at 50° C. under nitrogen for one hour, then allowed to cool. The solid is collected, washed with toluene and then with ether, giving 9.0 g. of a green-black solid, m.p. 105°-109° C.

We claim:

1. The method of inducing regression of leukemia and/or inhibiting growth of tumors in a mammal comprising administering to said mammal an effective antineoplastic amount of a compound selected from the group consisting of those of the formula:

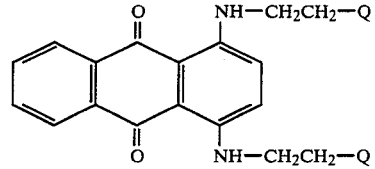

wherein Q is amino, methylamino, ethylamino, dimethylamino, or diethylamino, the leuco bases and tautomers thereof, and the pharmacologically acceptable acid-addition salts thereof.

* * * * *